US006962928B2

(12) United States Patent
Wallace

(10) Patent No.: US 6,962,928 B2
(45) Date of Patent: Nov. 8, 2005

(54) TETRAHYDROQUINOLINE DERIVATIVES FOR THE INHIBITION OF OSTEOPOROSIS, ESTROGEN DEPENDENT BREAST CANCER, ENDOMETRIOSIS AND UTERINE FIBROSIS

(75) Inventor: Owen Brendan Wallace, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/475,867
(22) PCT Filed: May 9, 2002
(86) PCT No.: PCT/US02/11879
§ 371 (c)(1), (2), (4) Date: Oct. 22, 2003
(87) PCT Pub. No.: WO02/094268
PCT Pub. Date: Nov. 28, 2002

(65) Prior Publication Data
US 2004/0132770 A1 Jul. 8, 2004

Related U.S. Application Data
(60) Provisional application No. 60/292,576, filed on May 22, 2001.

(51) Int. Cl.$^7$ ............... A61K 31/47; A61K 31/4709; A61K 31/5377
(52) U.S. Cl. ............... 514/311; 514/314; 514/235.2
(58) Field of Search ............... 514/311, 314, 514/235.2

(56) References Cited

U.S. PATENT DOCUMENTS

| | | | |
|---|---|---|---|
| 3,819,637 A | 6/1974 | Bell | |
| 3,994,902 A | 11/1976 | Bell | |
| 4,075,227 A | 2/1978 | Jones et al. | |
| 4,133,814 A | 1/1979 | Jones et al. | |
| 4,230,862 A | 10/1980 | Suarez et al. | |
| 4,418,068 A | 11/1983 | Jones | |
| 5,393,763 A | 2/1995 | Black et al. | |
| 5,403,847 A | 4/1995 | Gluchowski et al. | |
| 5,446,053 A | 8/1995 | Keohane | |
| 5,457,116 A | 10/1995 | Black et al. | |
| 5,461,065 A | 10/1995 | Black et al. | |
| 5,482,949 A | 1/1996 | Black et al. | |
| 5,508,306 A | 4/1996 | Chiu et al. | |
| 5,510,357 A | 4/1996 | Palkowitz | |
| 5,523,309 A | 6/1996 | Bryant et al. | |
| 5,567,828 A | 10/1996 | Dodge | |
| 5,686,465 A | 11/1997 | Yves et al. | |
| 5,688,796 A | 11/1997 | Cullinan et al. | |
| 5,693,345 A | 12/1997 | Chen et al. | |
| 5,723,474 A | 3/1998 | Palkowitz | |
| 5,726,168 A | 3/1998 | Cullinan et al. | |
| 5,728,724 A | 3/1998 | Bryant et al. | |
| 5,811,421 A | 9/1998 | Dodge et al. | |
| 5,840,735 A | 11/1998 | Labrie et al. | |
| 5,843,963 A | 12/1998 | Hauser et al. | |
| 5,843,965 A | 12/1998 | Palkowitz | |
| 5,916,916 A | 6/1999 | Hauser et al. | |
| 5,929,090 A | 7/1999 | Hauser et al. | |
| 5,948,795 A | 9/1999 | Berg et al. | |
| 5,948,796 A | 9/1999 | Bryant et al. | |
| 5,958,916 A | 9/1999 | Bryant et al. | |
| 5,958,969 A | 9/1999 | Bryant et al. | |
| 5,962,475 A | 10/1999 | Schmid et al. | |
| 5,981,570 A | 11/1999 | Bryant et al. | |
| 5,985,897 A | 11/1999 | Muehl et al. | |
| 5,998,401 A | 12/1999 | Palkowitz | |
| 5,998,442 A | 12/1999 | Yong Cho et al. | |
| 6,017,914 A | 1/2000 | Bryant et al. | |
| 6,025,382 A | 2/2000 | Bastian et al. | |
| 6,060,488 A | 5/2000 | Dodge et al. | |
| 6,090,843 A | 7/2000 | Bryant et al. | |
| 6,303,634 B1 | 10/2001 | Cohen et al. | |

(Continued)

FOREIGN PATENT DOCUMENTS

| | | |
|---|---|---|
| EP | 0 773 217 A1 | 5/1997 |
| EP | 0 802 183 A1 | 10/1997 |
| EP | 0 802 184 A1 | 10/1997 |
| EP | 0 747 380 B1 | 9/1998 |
| EP | 0 729 951 B1 | 6/1999 |
| EP | 1 113 007 | 7/2001 |
| JP | 04 316557 | 11/1992 |
| WO | WO 95/10513 | 4/1995 |
| WO | WO 95/17382 | 6/1995 |

(Continued)

OTHER PUBLICATIONS

XP002170868; "Structure–Activity–Relationship of Antiestrogens. Effect of the Side Chain and Its Position on the Activity of 2,3–Diaryl–2H–1–Benzopyrans"; Sharma, A.P., et al; Journal of Medicinal Chemistry, American Chemical Society, Washington, U.S.; vol. 33; 1990; pp. 3216–3222.

Primary Examiner—Phyllis G. Spivack
(74) Attorney, Agent, or Firm—Gilbert T. Voy; William R. Boudreaux

(57) ABSTRACT

The current invention provides methods for inhibiting osteoporosis, estrogen dependent breast cancer, endometriosis and uterine fibrosis comprising administering to a patient in need thereof a compound of the formula:

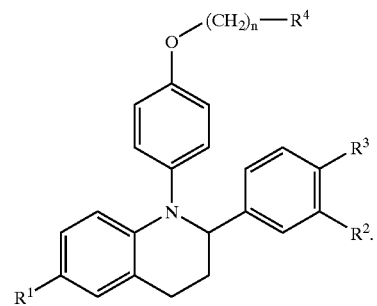

32 Claims, No Drawings

U.S. PATENT DOCUMENTS

| | | |
|---|---|---|
| 6,384,053 B1 | 5/2002 | Muehl |
| 6,391,892 B1 | 5/2002 | Bryant et al. |
| 6,395,755 B1 | 5/2002 | Bryant et al. |
| 6,399,634 B1 | 6/2002 | Bryant et al. |
| 6,410,564 B1 | 6/2002 | Bryant et al. |
| 6,417,199 B1 | 7/2002 | Muehl |
| 6,432,982 B1 | 8/2002 | Cullinan et al. |
| 6,432,983 B1 | 8/2002 | Cullinan et al. |
| 6,440,958 B1 | 8/2002 | Jones et al. |
| 6,444,688 B1 | 9/2002 | Dodge et al. |
| 6,479,517 B1 | 11/2002 | Bryant et al. |
| 6,509,356 B1 | 1/2003 | Dodge et al. |
| 6,599,920 B2 | 7/2003 | Bryant et al. |
| 6,608,090 B1 | 8/2003 | Bourgeois et al. |

FOREIGN PATENT DOCUMENTS

| | | |
|---|---|---|
| WO | WO 96/32937 | 10/1996 |
| WO | WO 97/25033 | 7/1997 |
| WO | WO 98 08797 | 3/1998 |
| WO | 0 835 867 A1 | 4/1998 |
| WO | WO 98/48793 | 11/1998 |
| WO | WO 99/19293 | 4/1999 |
| WO | WO 99/59969 | 11/1999 |

TETRAHYDROQUINOLINE DERIVATIVES FOR THE INHIBITION OF OSTEOPOROSIS, ESTROGEN DEPENDENT BREAST CANCER, ENDOMETRIOSIS AND UTERINE FIBROSIS

This application claims the benefit under 35 U.S.C. §120 of International Application No. PCT/US02/11879 filed May 9, 2002, which claims the benefit under 35 U.S.C. §119(e) of U.S. Ser. No. 60/292,576, filed May 22, 2001.

BACKGROUND OF THE INVENTION

The present invention relates to methods of inhibiting diseases associated with estrogen deprivation or with an aberrant physiological response to endogenous estrogen using 2-substituted 1,2,3,4-tetrahydroquinolines and derivatives thereof.

Menopause, the transition in women from the reproductive to the non-reproductive stage of life, is characterized by the cessation of menstruation and occurs at an average age of fifty years. The postmenopausal state is characterized by changes in the levels of circulating sex hormones, the most dramatic of which is the reduction in plasma levels of 17β-estradiol to less than ten percent of premenopausal values. Clinical and epidemiological studies have shown that the postmenopausal state is an important risk factor for a number of chronic disorders, notably osteoporosis and cardiovascular disease. In view of the fact that the current life span of women is about eighty years, women spend approximately one-third of their lives in the postmenopausal state. This means that the potential for chronic effects of the postmenopausal state on women's health is greater today than at the turn of the century when life expectancy was considerably shorter.

Osteoporosis describes a group of diseases which are characterized by the net loss of bone mass per unit volume. The consequence of this loss of bone mass and resulting bone fracture is the failure of the skeleton to provide adequate structural support for the body. The most vulnerable bone tissue to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which inter-connect with each other, as well as the more solid and dense cortical tissue which makes up the outer surface and central shaft of the bone. This inter-connected network of trabeculae gives lateral support to the outer cortical structure and is critical to the biomechanical strength of the overall structure.

Following the cessation of menses, most women lose from about 20% to about 60% of the bone mass in the trabecular compartment of the bone within 3 to 6 years. This rapid loss is generally associated with an increase of bone resorption and formation. However, the resorptive cycle is more dominant and the result is a net loss of bone mass.

In postmenopausal osteoporosis, it is primarily the net resorption and loss of the trabeculae which leads to the failure and fracture of bone. In light of the loss of the trabeculae in postmenopausal women, it is not surprising that the most common fractures are those associated with bones which are highly dependent on trabecular support, for example the vertebrae, the neck, and the weight bearing bones such as the femur and the fore-arm. Indeed, hip fracture, collies fractures, and vertebral crush fractures are hallmarks of postmenopausal osteoporosis.

There are an estimated 25 million women in the United States alone who are afflicted with this disease. The results of osteoporosis are personally harmful and also account for a large economic loss due its chronicity and the need for extensive and long term support (hospitalization and nursing home care). This is especially true in more elderly patients. Additionally, although osteoporosis is not generally thought of as a life threatening condition, a 20% to 30% mortality rate is related with hip fractures in elderly women. A large percentage of this mortality rate can be directly associated with postmenopausal osteoporosis.

At the present time, one generally accepted method for treatment of disorders resulting in the postmenopausal state from the decline in estrogen levels is estrogen replacement therapy. The therapy may take the form of administering estrogen alone in so-called unopposed estrogen replacement therapy (ERT) or in the form of coadministering estrogen and progestin in a so-called hormonal replacement therapy (HRT) regimen. There are, however, major liabilities associated with chronic administration of estrogen in postmenopausal women having to do with adverse effects on the breast and uterus. Women on ERT develop endometrial cancer at rates three to six times higher than nonusers after three to six years of use; after ten years of ERT, the risk ratio increases to tenfold.

To combat these deleterious effect of ERT, the coadministration of progestin along with estrogen in a combined hormonal replacement therapy (HRT) is employed, since progestin acts to limit uterine stimulation and thus reduce the risk of uterine cancer.

Because of these known and suspected or feared liabilities of estrogen therapy, prescription of and patient compliance with chronic estrogen replacement therapy has been poor. It has been estimated that, in the United States among postmenopausal women for whom ERT or HRT has been prescribed, fewer than forty percent continue therapy beyond one year.

As a consequence, there is a need for the development of postmenopausal therapy agents which possess the ideal pharmacological profile: for example agents which produce the beneficial effects of estrogen upon skeletal tissue and the cardiovascular system without producing the adverse effects of estrogen upon the breast and the uterus. Agents possessing such an estrogen profile would reverse the effects of estrogen deficiency in certain tissues while at the same time bypassing or failing to act in tissues in which estrogen produces adverse effects. The term selective estrogen receptor modulators or "SERMs" has been applied such compounds which possess this tissue selective profile. SERMs are defined as compounds producing estrogen agonism in one or more desired target tissues such as bone, liver, etc., together with estrogen antagonism and/or minimal (i.e. clinically insignificant) agonism in reproductive tissues such as the breast or uterus.

BRIEF SUMMARY OF THE INVENTION

The present invention provides a method for inhibiting a disease associated with estrogen deprivation comprising administering to a patient in need thereof a therapeutically effective amount of a compound of the formula

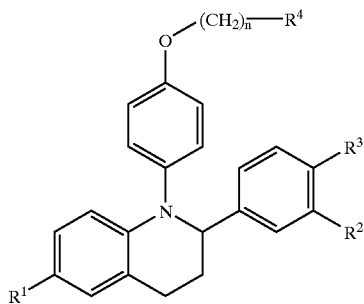

wherein
R$^1$ is —H, —OH, —O(C$_1$–C$_4$ alkyl), —OCOC$_6$H$_5$, —OCO(C$_1$–C$_6$ alkyl), or —OSO$_2$(C$_2$–C$_6$ alkyl);
R$^2$ and R$^3$ are each independently —H, —OH, —O(C$_1$–C$_4$ alkyl), —OCOC$_6$H$_5$, —OCO(C$_1$–C$_6$ alkyl), —OSO$_2$(C$_2$–C$_6$ alkyl) or halo;
R$^4$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;
n is 1, 2 or 3;
or a pharmaceutically acceptable salt thereof.

In an alternative embodiment of the medical method of the present invention, the compounds of the present invention are employed in the treatment of disease conditions associated with an aberrant physiological response to endogenous estrogen including uterine fibroid disease or uterine fibrosis, endometriosis, and estrogen dependent cancers.

DETAILED DESCRIPTION OF THE INVENTION

General terms used in the description of compounds herein described bear their usual meanings. For example, "C$_1$–C$_6$ alkyl" refers to straight or branched aliphatic chains of 1 to 6 carbon atoms including moieties such as methyl, ethyl, propyl, isopropyl, butyl, n-butyl, pentyl, isopentyl, hexyl, isohexyl, and the like. Likewise, "C$_1$–C$_4$ alkyl" refers to straight or branched aliphatic chains of 1 to 4 carbon atoms including moieties such as methyl, ethyl, propyl, isopropyl, butyl, n-butyl, and the like. Similarly, the term "C$_1$–C$_4$ alkoxy" represents a C$_1$–C$_4$ alkyl group attached through an oxygen molecule and include moieties such as, for example, methoxy, ethoxy, n-propoxy, isopropoxy, and the like.

The term "halo" refers to bromo, chloro, fluoro and iodo.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein E$^1$ is the amount of the first enantiomer and E$^2$ is the amount of the second enantiomer. Thus, if the initial ratio of the two enantiomers is 50:50, such as is present in a racemic mixture, and an enantiomeric enrichment sufficient to produce a final ratio of 70:30 is achieved, the ee with respect to the first enantiomer is 40%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of formula I can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

The designation "  " refers to a bond that protrudes forward out of the plane of the page.

The designation "  " refers to a bond that protrudes backward out of the plane of the page.

The designation "  " refers to a bond wherein the stereochemistry is not defined.

As used herein, the term "estrogen" includes steroidal compounds having estrogenic activity such as, for example, 17β-estradiol, estrone, conjugated estrogen (Premarin®), equine estrogen 17a-ethynyl estradiol, and the like. As used herein, the term "progestin" includes compounds having progestational activity such as, for example, progesterone, norethylnodrel, nongestrel, megestrol acetate, norethindrone, and the like.

Preferred compounds of this invention include compounds of formula I wherein $R^4$ is 1-pyrrolidinyl or 1-piperidinyl. A further preferred subgroup of the preferred 1-pyrrolidinyl or 1-piperidinyl compounds include those compounds wherein $R^1$, $R^2$, and $R^3$ are each independently —H, —OH or —OCH$_3$.

Particularly preferred compounds of formula I include those having all of the aforementioned limitations, that is, compounds wherein $R^1$, $R^2$, and $R^3$ are each independently —H, —OH, or —OCH$_3$, particularly wherein $R^1$ and $R^2$ are —OH and $R^3$ is —H or wherein $R^1$ and $R^3$ are —OH and $R^2$ is —H; $R^4$ is 1-pyrrolidinyl or 1-piperidinyl; and n is 2.

Although the free-base or acid forms of formula I compounds can be used in the methods of the present invention, it is preferred to prepare and use a pharmaceutically acceptable salt form. Thus, the compounds used in the methods of this invention form pharmaceutically acceptable acid or base addition salts with a wide variety of organic and inorganic acids and bases, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, b-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. Preferred salts are the hydrochloride and oxalate salts.

Typical bases used to form pharmaceutically acceptable addition salts would be inorganic bases, such as, sodium hydroxide, potassium hydroxide, alkali carbonates or bicarbonates, calcium carbonate, magnesium carbonate, and the like. Additionally, organic bases may be utilized to form addition salts, e.g., alkyl amines, such as, triethylamine, dimethylamine, i-propylamine, and the like.

The pharmaceutically acceptable acid or base addition salts are typically formed by reacting a compound of formula I with an equimolar or excess amount of acid or base. The reactants are generally combined in a mutual solvent such as diethyl ether or ethyl acetate. The salt normally precipitates out of solution within about one hour to 10 days and can be isolated by filtration or the solvent can be stripped off by conventional means.

Specific examples of compounds contemplated as falling within the scope of the Formula I compounds include, but are not limited to the following compounds and their pharmaceutically acceptable salts:

1-(4-hydroxy-phenyl)-1-[4-(2-piperidin-1-yl-ethoxy)-phenyl]-1,2,3,4-tetrahydro-quinolin-6-ol;
1-(4-hydroxy-phenyl)-1-[4-(2-pyrrolidin-1-yl-ethoxy)-phenyl]-1,2,3,4-tetrahydro-quinolin-6-ol;
1-(3-hydroxy-phenyl)-1-[4-(2-piperidin-1-yl-ethoxy)-phenyl]-1,2,3,4-tetrahydro-quinolin-6-ol;
1-(3-hydroxy-phenyl)-1-[4-(2-pyrrolidin-1-yl-ethoxy)-phenyl]-1,2,3,4-tetrahydro-quinolin-6-ol;
1-(4-hydroxy-phenyl)-1-[4-(2-piperidin-1-yl-ethoxy)-phenyl]-1,2,3,4-tetrahydro-quinolin-6-ol;
1-(4-hydroxy-phenyl)-1-[4-(2-pyrrolidin-1-yl-propoxy)-phenyl]-1,2,3,4-tetrahydro-quinolin-6-ol;
1-(3-hydroxy-phenyl)-1-[4-(2-piperidin-1-yl-propoxy)-phenyl]-1,2,3,4-tetrahydro-quinolin-6-ol;
6-methoxy-2-(4-methoxy-phenyl)-1-[4-(2-piperidin-1-yl-ethoxy)-phenyl]-1,2,3,4-tetrahydro-quinoline;
6-methoxy-2-(4-methoxy-phenyl)-1-[4-(2-pyrrolidin-1-yl-ethoxy)-phenyl]-1,2,3,4-tetrahydro-quinoline;
6-methoxy-2-(3-methoxy-phenyl)-1-[4-(2-piperidin-1-yl-ethoxy)-phenyl]-1,2,3,4-tetrahydro-quinoline;
6-methoxy-2-(3-methoxy-phenyl)-1-[4-(2-pyrrolidin-1-yl-ethoxy)-phenyl]-1,2,3,4-tetrahydro-quinoline;
6-methoxy-2-(4-methoxy-phenyl)-1-[4-(2-piperidin-1-yl-propoxy)-phenyl]-1,2,3,4-tetrahydro-quinoline; and
6-methoxy-2-(4-methoxy-phenyl)-1-[4-(2-pyrrolidin-1-yl-propoxy)-phenyl]-1,2,3,4-tetrahydro-quinoline.

The compounds of formula (I) can be prepared by utilizing procedures and techniques well known and appreciated by one of ordinary skill in the art. For example, some of the compounds of formula (I) are disclosed in U.S. Pat. No. 3,994,902, incorporated by reference herein as if fully set forth. Alternatively, a general synthetic scheme for preparing compounds of formula (I) is set forth in Scheme A, wherein all substituents, unless otherwise indicated, are previously defined.

SCHEME A

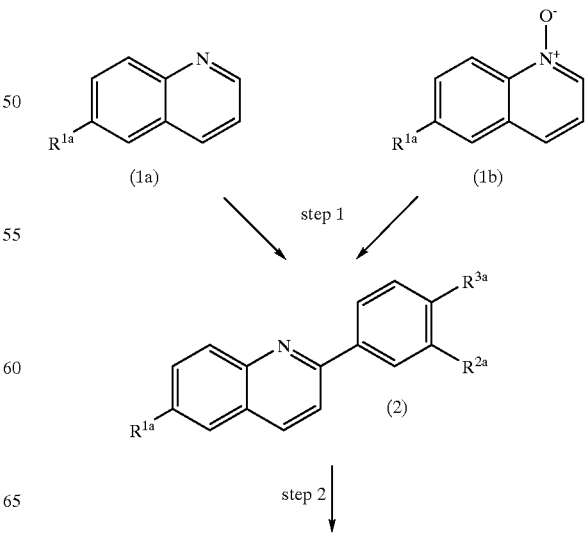

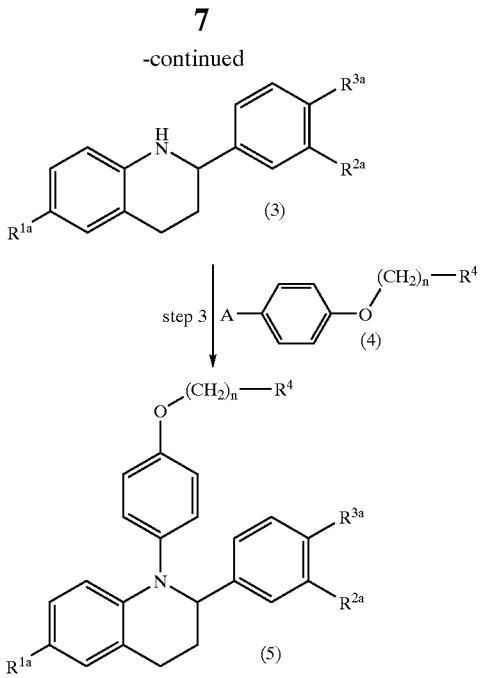

In Scheme A, $R^{1a}$, $R^{2a}$, and $R^{3a}$ are each independently —H, —OH, or —OPg, where Pg is a hydroxy protecting group; and A is a suitable activating group defined more fully below. In compounds of formula (1a), (1b), (2), (3), et seq., the Pg protecting groups $R^{1a}$, $R^{2a}$, and $R^{3a}$ are phenolic protecting groups of the type taught by T. Greene, et al. in Chapter 3 of "Protective Groups in Organic Synthesis," Second Edition, John Wiley & Sons, Inc., New York, 1991, pp.143–170. The preferred protecting groups are alkyl ether groups, with methyl being particularly preferred.

In Scheme A, step 1, the 2-phenylquinoline of formula (2) may be prepared by either reacting $R^{1a}$-substituted quinoline of formula (1a) with a $R^{2a}$, $R^{3a}$-substituted phenyl lithium or $R^{1a}$-substituted quinoline-N-oxide (1b) with a $R^{2a}$, $R^{3a}$-substituted phenyl magnesium halide under Grignard conditions. The Grignard reaction and the reactions using organolithium compounds are of the type taught by Gilman et al., *J. Am. Chem. Soc.* 68, 2017 (1946); Gilman and Gainer, *J. Am. Chem. Soc.* 69, 887 (1947); and Comins, D. L., Brown, J. D., *Tetrahedron Lett.* 27, 4549 (1986).

For example, the $R^{1a}$-substituted quinoline-N-oxide (1b) is reacted with methyl chloroformate at a temperature range of from about −90° C. to about −50° C., more preferably about −78° C. The reaction is typically conducted under anhydrous conditions in a suitable aprotic organic solvent such as anhydrous tetrahydrofuran. The $R^{1a}$-substituted quinoline-N-oxide (1b) and the methyl chloroformate are preferably present in the reaction zone in an approximately equimolar quantity. A slight excess of either reactant is not detrimental to the reaction. The reaction is allowed to proceed for a period of time ranging from about 20 minutes to about 5 hours. A substantially equimolar amount of $R^{2a}$, $R^{3a}$-substituted phenyl magnesium halide is then added. The reaction is then quenched with a proton source such as, for example, sodium bicarbonate or methanol. The solvent is removed and the resulting mixture is extracted, concentrated and purified according to techniques well known in the art.

Appropriate $R^{1a}$-substituted quinolines of formula (1a) and appropriate $R^{1a}$-substituted quinoline-N-oxides (1b) are commercially available or are prepared by techniques and procedures well known in the art.

Further, appropriate $R^{2a}$, $R^{3a}$-substituted phenyl lithiums and $R^{2a}$, $R^{3a}$-substituted phenyl magnesium halides are commercially available or prepared by techniques well known in the art. For example, a solution of the appropriate $R^{2a}$, $R^{3a}$-substituted phenyl is reacted with an organolithium compound such as n-butyllithium or t-butyllithium, more preferably t-butyllithium, for a period of time ranging from about 5 minutes to about 30 minutes and more preferably about 15 minutes; at a temperature range of from about −90° C. to about −50° C., more preferably about −78° C. The organolithium compound will be present in the quantity of from about 1.0 to 1.1 equivalents for every mole of $R^{2a}$, $R^{3a}$-substituted phenyl utilized, and more preferably will be present in an approximately equimolar quantity. The reaction is typically conducted under anhydrous conditions in a suitable aprotic organic solvent such as tetrahydrofuran.

In Scheme A, step 2, the 2-phenyl-1,2,3,4-tetrahydroquinoline of formula (3) is prepared by reducing 2-phenylquinoline of formula (2). For example, 2-phenylquinoline of formula (2) is dissolved in a suitable alcoholic solvent, such as absolute ethanol. Sodium metal is then added and the reaction is allowed to cool to room temperature. The reaction mixture may then be diluted with water and extracted with a suitable organic solvent, such as methylene chloride, ethyl acetate, or chloroform. The combined extracts may then be washed with water and brine, the organic layer is separated and dried and the solvent is evaporated in vacuo to provide the 2-phenyl-1,2,3,4-tetrahydroquinoline of formula (3) which may be used without further purification.

Alternatively, reduction of 2-phenylquinoline of formula (2) may be attained using sodium borohydride in ethanol with nickel chloride catalyst, in a method analogously described by Nose and Kudo, *Chem. Pharm. Bull.* 36, 1529 (1988).

In Scheme A, step 3, the 1,2-disubstituted-1,2,3,4-tetrahydroquinoline of formula (5) may be prepared by arylating the 2-phenyl-1,2,3,4-tetrahydroquinoline of formula (3) with the substituted benzoyl derivative of compound (4).

For example, the 2-disubstituted-1,2,3,4-tetrahydroquinoline of formula (5) may be prepared by arylating the 2-phenyl-1,2,3,4-tetrahydroquinoline of formula (3) with the substituted halide derivative of compound (4) according to the procedures set forth in Hartwig, J. F. et al., "Room Temperature Palladium-Catalyzed Amination of Aryl Bromides and Chlorides and Extended Scope of Aromatic Bond Formation with a Commercial Ligand", *J. Org. Chem.* 64, 5575–5580 (1999).

Appropriate compounds of formula (4) can be prepared as described as set forth analogously in PCT Intnl. Appl. Publ. No. WO 98/48793, published Nov. 5, 1998, the disclosure of which is hereby incorporated by reference.

In compounds of formula (4), the activating group, A, is selected from groups well known in the art to activate aromatic compounds for the purposes of carrying out coupling reactions and include halides such as the chloride, bromide, or iodide.

When a —OC(O)($C_1$–$C_6$ alkyl) or —OC(O)$C_6H_5$ group is desired at $R^1$, $R^2$, and/or $R^3$ a mono-, di-, or trihydroxy compound of formula I, is reacted with an agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger, such as a tertiary amine, has been added. If desired, acylation catalysts such as 4-dimethylaminopyridine or 4-pyrrolidinopyridine may be used. See, e.g., Haslam, et al., *Tetrahedron*, 36:2409–2433 (1980).

The acylation reactions which provide the aforementioned $R^1$, $R^2$, and/or $R^3$ groups are carried out at moderate temperatures in the range from about –25° C. to about 100° C., frequently under an inert atmosphere such as nitrogen gas. However, ambient temperature is usually adequate for the reaction.

Such acylations of the hydroxy group also may be performed by acid-catalyzed reactions of the appropriate carboxylic acids in inert organic solvents or neat. Acid catalysts such as sulfuric acid, polyphosphoric acid, methanesulfonic acid, and the like are used.

The aforementioned $R^1$, $R^2$, and/or $R^3$ groups also may be provided by forming an active ester of the appropriate acid, such as the esters formed by such known reagents as dicyclohexylcarbodiimide, acylimidazoles, nitrophenols, pentachlorophenol, N-hydroxysuccinimide, and 1-hydroxybenzotriazole. See, e.g., *Bull. Chem. Soc. Japan*, 38:1979 (1965), and *Chem. Ber.*, 788 and 2024 (1970).

When a compound is desired in which $R^1$, $R^2$, and/or $R^3$ are —$OSO_2(C_4-C_6$ alkyl), the suitable starting mono-, di- or trihydroxy compound is reacted with, for example, a derivative of the appropriate sulfonic acid such as a sulfonyl chloride, bromide, or sulfonyl ammonium salt, as taught by King and Monoir, *J. Am. Chem. Soc.*, 97:2566–2567 (1975). The mono-, di- or trihydroxy compound also can be reacted with the appropriate sulfonic anhydride. Such reactions are carried out under conditions such as were explained above in the discussion of reaction with acid halides and the like.

Compounds of formula I can be prepared so that $R^1$, $R^2$, and/or $R^3$ are different biological protecting groups or, preferably, the same biological protecting group. Preferred protecting groups include —$CH_3$, —$C(O)C(CH_3)_3$, —$C(O)C_6H_5$, and —$SO_2(CH_2)_3CH_3$.

EXAMPLES

All reactions are carried out under a nitrogen atmosphere. All solvents are ACS grade and are used as supplied. All reagents are commercially available and used without further purification unless otherwise noted. LCMS data is recorded on a Hewlett Packard 1100 series at 35° C. The method used is 5% acetonitrile—95% water (0.05% TFA) to 95% acetonitrile—5% water (0.05% TFA) over two minutes and hold for three minutes on a Waters Symmetry C18 2.1×50 mm column. $^1$H NMR spectra are recorded at 400 MHz on a Varian 400 spectrometer in $CDCl_3$ ($\partial$ 7.26) unless otherwise noted.

Preparation 1

6-Methoxy-2-(4-methoxy-phenyl)-quinoline

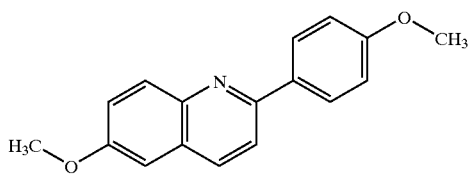

A 500 mL round-bottom flask is charged with 6-methoxy quinoline-N-oxide (8 g, 0.04566 mol.) and placed under nitrogen. The solid is then dissolved in anhydrous THF (100 mL) and cooled to –78° C. with a dry ice/acetone bath, whereupon some of the dissolved solid begins to precipitate. From an addition funnel, methylchloroformate (4.4 ml, 0.05694 mol.) is added dropwise. The bath is removed 10 minutes after the addition, and replaced after 20 minutes. A dropwise addition of 0.5 M anisylmagnesium bromide (112 mL, 0.0560 mol.) is then made. The bath is removed after the addition and the reaction is allowed to warm to room temperature. The reaction is quenched with 5% sodium bicarbonate solution. The THF is removed in vacuo and the resulting mixture is diluted with water and extracted with methylene chloride. The extracts are collected and dried with anhydrous sodium sulfate and concentrated. The crude product is purified by flash chromatography (2–5% EtOAc/dichloromethane) to yield 6.30 g (52%) of the desired product. $^1$H NMR: $\partial$ 8.03–8.11 (m, 4H), 7.78 (d, J=8.8 Hz, 1H), 7.37 (dd, J=9 Hz, 3 Hz, 1H), 7.03–7.07 (m, 3H), 3.94 (s, 1H), 3.88 (s, 1H). LCMS: 2.188 min, 266 (M+).

Preparation 2

6-Methoxy-2-phenyl-quinoline

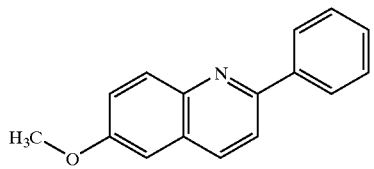

6-Methoxy-2-phenyl quinoline is prepared in a manner analogous to that of Preparation 1 using phenyl magnesium bromide. $^1$H NMR: $\partial$ 8.07–8.15 (m, 4H), 7.84 (d, J=8.8 Hz, 1H), 7.50–7.54 (m, 2H), 7.42–7.46 (m, 1H), 7.39 (dd, J=9 Hz, 3 Hz, 1H), 7.10 (d, J=2.4 Hz, 1H), 3.95 (s, 3H).

Preparation 3

6-Methoxy-2-(4-methoxyphenyl)-1,2,3,4-tetrahydroquinoline

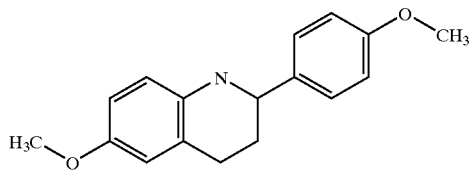

A 500 mL round-bottom flask is charged with the compound of Preparation 1 (3 g, 0.01131 mol) and absolute ethanol (150 mL). The mixture is placed under nitrogen and brought to reflux. Sodium metal pellets are added periodically until no starting material remains by TLC (30% EtOAc/hexanes). The reaction is cooled to room temperature, diluted with water, and extracted with methylene chloride. The combined extracts are then washed with water and brine. The organic is separated and dried with anhydrous sodium sulfate. The solvent is removed in vacuo to yield 3.05 g (100%) of a gold oil. No purification is necessary. $^1$H NMR: $\partial$ 7.32 (app. d, J=8.4 Hz, 2H), 6.89 (app. d, J=8.8 Hz, 2H), 6.61–6.65 (m, 2H), 6.49 (d, J=8.4 Hz, 1H), 4.31 (dd, J=10 Hz, 2.8 Hz, 1H), 3.81 (s, 3H), 3.75 (s, 3H), 2.90–2.99 (m, 1H), 2.73 (dt, J=16.4 Hz, 4.6 Hz, 1H), 2.04–2.10 (m, 1H), 1.91–2.01 (m, 1H).

Preparation 4

6-Methoxy-2-phenyl-1,2,3,4-tetrahydroquinoline

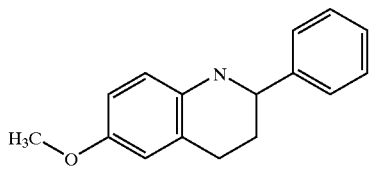

6-Methoxy-2-phenyl-1,2,3,4-tetrahydro-quinoline is prepared in a manner analogous to that of Preparation 3 using 6-Methoxy-2-phenyl quinoline. $^1$H NMR: $\partial$ 7.28–7.43 (m, 5H), 6.63–6.67(m, 2H), 6.52 (d, J=8.8 Hz, 1H), 4.38 (dd, J=9.0 Hz, 3.0 Hz, 1H), 3.76 (s, 3H), 2.91–3.00 (m, 1H), 2.74 (dt, J=16.8 Hz, 4.6 Hz, 1H), 2.09–2.15 (m, 1H), 1.95–2.05 (m, 1H).

Preparation 5

6-Methoxy-2-(3-methoxy-phenyl)-quinoline

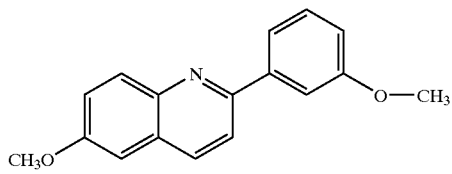

To a solution of 6-methoxyquinoline-N-oxide (175 mg, 1.0 mmol) in THF (3 mL) at room temperature is added methyl chloroformate (77 uL, 1.0 mmol). The mixture is cooled to 0° C. and 3-methoxyphenylmagnesium bromide (2 mL of 1M, 2 mmol) is added dropwise. The mixture is stirred for 16 h while warming to room temperature. The solvent is removed in vacuo and the resulting residue is partitioned between water and CH$_2$Cl$_2$. The organic phase is washed with water and brine, dried over MgSO$_4$, filtered and concentrated. Flash chromotography (0–20% EtOAc/hexanes) yields 6-methoxy-2-(3-methoxy-phenyl)-quinoline (123 mg, 46% yield).

$^1$H NMR: $\partial$ 3.90 (s, 3H), 3.92 (s, 3H), 6.97 (app. d, 1H), 7.08 (s, 2H), 7.38 (m, 2H), 7.65 (d, 1H), 7.71 (app. s, 1H), 7.81 (d, 1H), 8.10 (m, 2H).

Preparation 6

6-Methoxy-2-(3-methoxy-phenyl)-1,2,3,4-tetrahydro-quinoline

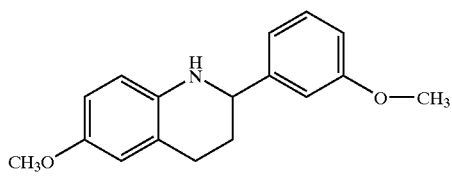

To a stirred solution of 6-methoxy-2-(3-methoxy-phenyl)-quinoline (96 mg, 0.36 mmol) in EtOH (3 mL) at 0° C. is added NiCl$_2$.6H$_2$O (86 mg, 0.36 mmol). The reaction mixture is stirred for 30 min before the addition of NaBH$_4$ (55 mg, 1.45 mmol). The mixture is stirred for 16 h while warming to room temperature. An additional portion of NaBH$_4$ (50 mg) is then added and stirring is continued for 3 h. The solvent is removed in vacuo and the resulting residue is partitioned between water and CH$_2$Cl$_2$. The organic phase is washed with water and brine, dried over MgSO$_4$, filtered and concentrated. Flash chromotography (0–50% EtOAc/hexanes) yields 6-methoxy-2-(3-methoxy-phenyl)-1,2,3,4-tetrahydro-quinoline.

$^1$H NMR: $\partial$ 1.95 (m, 1H), 2.08 (m, 1H), 2.71 (m, 1H), 2.2.90 (m, 2H), 3.7 s (s, 3H), 3.81 (s, 3H), 4.34 (dd, 1H), 6.50 (d, 2H), 6.71 (m, 2H), 6.81 (dd, 1H), 6.95 (m, 2H), 7.25 (m, 1H).

Example 1

6-Methoxy-2-(4-methoxy-phenyl)-1-[4-(2-piperidin-1-yl-ethoxy)-phenyl]-1,2,3,4-tetrahydro-quinoline

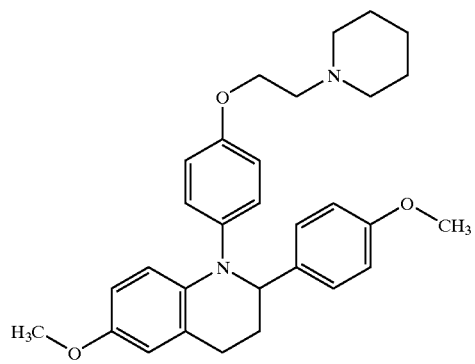

A 50 ml round bottom flask is charged with the compound of Preparation 3 (103.8 mg, 0.3854 mmol), 1-[2-(4-bromo-phenoxy)-ethyl]-piperidine (128.0 mg, 0.4504 mmol, PCT Intnl. Appl. Publ. No. WO 98/48793, published Nov. 5, 1998), sodium-t-butoxide (58.1 mg, 0.6045 mmol), palladium (II) acetate (10.1 mg, 0.04499 mmol), and dry toluene (15 ml). Several drops of tri-t-butylphosphine are added from a 1 ml insulin syringe. Two more additions of palladium (II) acetate (24.7 mg, 0.1100 mmol; 17.6 mg, 0.07840 mmol) are made in one hour intervals. Several drops of tri-t-butylphosphine are added after each palladium addition. The total amount added is 24.7 mg (0.1221 mmol). The reaction is followed by LC/MS. The reaction is filtered through silica with 0–10% MeOH/dichloromethane. The filtrate is concentrated and the crude product is purified by flash chromatography (1–5% MeOH/dichloromethane) to 90.3 mg (49.6%) as an oil. Some unknown impurities are present. The product is carried on without further purification. Partial $^1$H NMR: $\partial$ 7.16 (app. d, J=8.4 Hz, 2H), 7.01 (app. d, J=8.8 Hz, 2H), 6.74–6.79 (m, 4H), 6.53–6.62 (m, 3H), 4.72 (t, J=4.5 Hz, 1H), 4.11 (t, J=6 Hz, 2H), 3.75 (s, 3H), 3.72 (s, 3H), 2.18–2.27 (m, 1H), 2.04–2.12 (m, 1H). LCMS: 2.637 min., 473 (M+).

Example 2

6-Methoxy-2-(4-methoxy-phenyl)-1-[4-(2-pyrrolidin-1-yl-ethoxy)-phenyl]-1,2,3,4-tetrahydro-quinoline

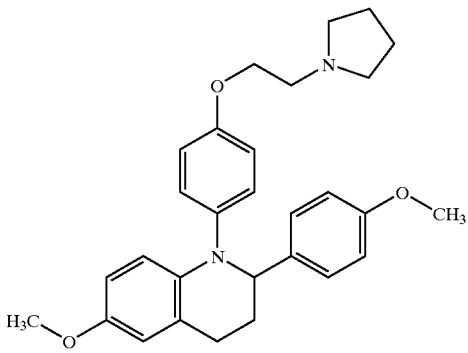

6-Methoxy-2-(4-methoxy-phenyl)-1-[4-(2-pyrrolidin-1-yl-ethoxy)-phenyl]-1,2,3,4-tetrahydro-quinoline is prepared in a manner analogous to that of Example 1 using 1-[2-(4-bromo-phenoxy)-ethyl]-pyrrolidine (PCT Intnl. Appl. Publ. No. WO 98/48793, published Nov. 5, 1998). $^1$H NMR: $\partial$ 7.17 (app. d, J=8.4 Hz, 2H), 7.04 (app. d, J=8.4 Hz, 2H), 6.79–6.81 (m, 4H), 6.58–6.64 (m, 3H), 4.74 (broad s, 1H), 4.18 (broad s, 2H), 3.77 (s, 3H), 3.74 (s, 3H), 3.05 (broad s, 2H), 2.85 (broad s, 4H), 2.19–2.27 (m, 1H), 2.05–2.17 (m, 1H), 1.91 (broad s, 6H). LCMS: 2.447 min, 459 (M+).

Example 3

1-(4-Hydroxy-phenyl)-1-[4-(2-piperidin-1-yl-ethoxy)-phenyl]-1,2,3,4-tetrahydro-quinolin-6-ol

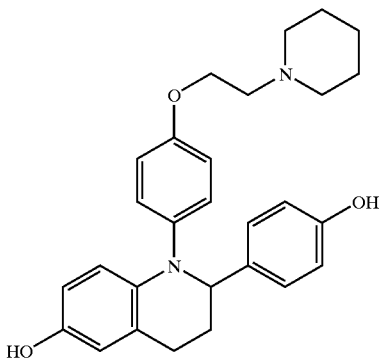

A 25 ml round-bottom flask is charged with the compound of Example 1 (90.3 mg, 0.1911) and dichloromethane (10 ml) The solution is placed under nitrogen and cooled to 0° C. before adding 1.0M boron tribromide in dichloromethane (0.90 ml, 0.90 mmol). The reaction is followed by LC/MS until completed. The reaction is quenched with methanol and preadsorbed onto silica gel. The crude product is then isolated by flash chromatography (1–10% MeOH/dichloromethane). The product is again chromatographed by preadsorbtion and flash chromatography (100% acetone). The resulting solid is crystallized from chloroform to yield 20.7 mg (24.4%) of the desired product. $^1$H NMR [CD$_3$OD ($\partial$ 3.30)]: $\partial$ 6.99 (d, J=8.8 Hz, 2H), 7.09 (d, J=8.8 Hz, 2H), 6.80 (d, J=8.8 Hz, 2H), 6.65 (d, J=8.8 Hz, 2H), 6.37–6.45 (m, 3H), 4.65 (t, J=4.6 Hz, 1H), 4.08 (t, J=6 Hz, 2H), 2.83 (app. s, 2H), 2.45–2.70 (m, 6H), 2.12–2.23 (m, 1H), 2.00–2.12 (m, 1H), 1.67 (m, 4H), 1.50 (broad s, 2H). LCMS: 2.177 min, 445 (M+).

Example 4

1-(4-Hydroxy-phenyl)-1-[4-(2-pyrrolidin-1-yl-ethoxy)-phenyl]-1,2,3,4-tetrahydro-quinolin-6-ol

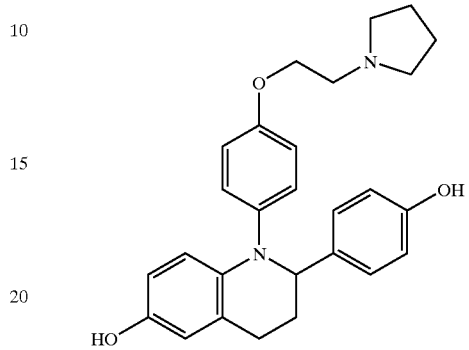

1-(4-Hydroxy-phenyl)-1-[4-(2-pyrrolidin-1-yl-ethoxy)-phenyl]-1,2,3,4-tetrahydro-quinolin-6-ol is prepared in a manner analogous to that of Example 3 using the compound of Example 2. The product is purified by reverse phase and is obtained as the TFA salt. $^1$H NMR [CD$_3$OD ($\partial$ 3.30)]: $\partial$ 7.02–7.08 (m, 4H), 6.88 (app. d, J=6.8 Hz, 2H), 6.65 (app. d, J=6.8 Hz, 2H), 6.46–6.49 (m, 2H), 6.39–6.40 (m, 1H), 4.67 (t, J=5.2 Hz, 1H), 4.25 (t, J=5 Hz, 2H), 3.66–3.74 (m, 2H), 3.60 (t, J=5 Hz, 2H), 3.16–3.22 (m, 2H), 2.62–2.72 (m, 1H), 2.50–2.58 (m, 1H), 2.16–2.22 (m, 3H), 2.02–2.09 (m, 3H). LCMS: 2.119 min., 431 (M+).

Biological Test Procedure General Preparation Procedure

ER Binding Assay

Competition binding assay is run in a buffer containing 50 mM Hepes, pH 7.5, 1.5 mM EDTA, 150 mM NaCl, 10% glycerol, 1 mg/ml ovalbumin and 5 mM DTT, using 0.025 µCi per well $^3$H-Estradiol (NEN #NET517 at 118 Ci/mmol, 1 mCi/ml), 10 ng/well ERAlpha or ERbeta receptor (PanVera). Competing compounds are added at 10 different concentrations. Non-specific binding is determined in the presence of 1 µM of 17-B Estradiol. The binding reaction (140 µl) is incubated for 4 hours at room temperature, then 70 µl of cold DCC buffer is added to each reaction (DCC buffer contains per 50 ml of assay buffer, 0.75 g of charcoal (Sigma) and 0.25 g of dextran (Pharmacia)). Plates are mixed 8 minutes on an orbital shaker at 4° C. Plates are then centrifuged at 3,000 rpm at 4° C. for 10 minutes. An aliquot of 120 µl of the mix is transferred to another 96-well, white flat bottom plate (Costar) and 175 µl of Wallac Optiphase "Hisafe 3" scintillation fluid is added to each well. Plates are sealed and shaken vigorously on an orbital shaker. After an incubation of 2.5 hrs, read plates in a Wallac Microbeta counter. The data is used to calculate an IC50 and % Inhibition at 10 µM. The Kd for $^3$H-Estradiol is determined by saturation binding to ER alpha and ER beta receptors. The IC$_{50}$ values for compounds are converted to K$_i$ using Cheng-Prusoff equation and the K$_d$ determined by saturation binding assay.

Ishikawa Alkaline Phosphatase Assay

Ishikawa human endometrial tumor cells are maintained in MEM (minimum essential medium, with Earle's salts and L-Glutamine, Gibco BRL, Gaithersburg, Md.), supplemented with 10% fetal bovine serum (FBS) (V/V), (Gibco BRL). One day prior to assay, growth media is changed to assay medium, DMEM/F-12 (3:1) (Dulbecco's Modified Eagle Medium: Nutrient Mixture F-12, 3:1 Mixture, phenol red-free, Gibco BRL) supplemented with 5% dextran coated charcoal stripped fetal bovine serum (DCC-FBS) (Hyclone, Logen, Utah), L-Glutamine (2 mM), MEM sodium pyruvate (1 mM), HEPES (N-[2-hydroxyethyl]piperazine-N'-[2-ethanesulfonic acid] 2 mM) all from Gibco BRL). After an overnight incubation, ishikawa cells are rinsed with Dulbecco's Phosphate Buffered Saline (1×) (D-PBS) without $Ca^{+2}$ and $Mg^{+2}$ (Gibco BRL), and trypsinized by a 3 minute incubation with 0.25% Trypsin/EDTA, phenol red-free (Gibco BRL). Cells are resuspended in assay medium and adjusted to 250,000 cells/ml. Approximately 25,000 cells in a 100 ul media are added to flat-bottom 96 wells microculture plates (Costar 3596) and incubated at 37° C. in a 5% $CO_2$ humidified incubator for 24 hours. The next day, serial dilutions of compounds are prepared in assay medium (at 6 times the final concentration in the assay). The assay is run in dual mode, agonist and antagonist modes. For the agonist mode, plates receive 25 $\mu$l/well of assay medium followed by 25 $\mu$l/well of diluted compounds (at 6× the final concentrations). For the antagonist mode, plates receive 25 $\mu$l/well of 6 nM $E_2$ ($\beta$-Estradiol, Sigma, St. Louis, Mo.) followed by 25 $\mu$l/well of diluted compounds (at 6× the final concentrations). After an additional 48-hour incubation at 37° C. in a 5% $CO_2$ humidified incubator, media is aspirated from wells and 100 $\mu$l fresh assay medium is added to each microculture. Serial dilutions of compounds are prepared and added to the cells as described above. After an additional 72 hour incubation at 37° C. in a 5% $CO_2$ humidified incubator, the assay is quenched by removing media and rinsing plates twice in Dulbecco's Phosphate Buffered Saline (1×) (D-PBS) (Gibco BRL). The plates are dried for 5 min and frozen at −70° C. for at least 1 hour. The plates are then removed from the freezer and allowed to thaw at room temperature. To each well, 100 $\mu$l of 1-Step™ PNPP (Pierce Chemical Company, Rockford, Ill.) is added. After a 20-minute incubation, plates are read on a spectophotometer at 405 nm. The data is fitted to a linear interpolation to derive EC50 (for agonist mode) or IC50 (for antagonist mode) values. For the agonist mode, a % efficacy for each compound is calculated versus the response to Tamoxifen. For the antagonist mode, a % efficacy for each compound is calculated versus E2 (1 nM) alone.

MCF-7 Proliferation Assay

MCF-7 breast adenocarcinoma cells (ATCC HTB 22) are maintained in MEM (minimal essential medium, phenol red-free, Gibco BRL) supplemented with 10% fetal bovine serum (FBS) (V/V), L-glutamine (2 mM), sodium pyruvate (1 mM), HEPES ((N-[2-hydroxyethyl]piperazine-N'-[2-ethanesulfonic acid]10 mM}, non-essential amino acids (0.1 mM) and Penicillin Streptomycin (1×). Seven days prior to assay, MCF-7 cells are switched to assay media which is the same as maintenance medium except supplemented with 10% dextran-coated charcoal-stripped fetal bovine serum (DCC-FBS) assay medium in place of 10% FBS. MCF-7 cells are removed from flasks using 10× Trypsin EDTA (phenol red free, Gibco BRL) and diluted to 1× in (Ca++/Mg++ free HBSS (phenol red-free). Cells are adjusted to 80,000 cells/ml in assay medium. Approximately 8,000 cells (100 $\mu$l) are added to each well in 96 well Cytostar T scintillation plates (Amersham) and incubated at 37° C. in a 5% $CO_2$ humidified incubator for 24 hours to allow cell adherence and equilibration after transfer. Serial dilutions of drugs are prepared in assay medium at 4× the final desired concentration). A 50 $\mu$l aliquot of drug dilutions (at 4× the final assay concentration) is transferred to duplicate wells followed by 50 $\mu$l assay medium for the agonist mode or 50 $\mu$l of 40 pM of E2 for the antagonist mode to a final volume of 200 $\mu$l. For each of the agonist plates, a basal level (media) and a maximum stimulated level (with 1 $\mu$M E2) is determined. For each of the antagonist plates, a basal level (media) and a E2 (10 pM) alone control is determined. After an additional 48 hours at 37° C. in a 5% $CO_2$ humidified incubator, 20 $\mu$l of assay medium containing 0.01 $\mu$Ci of $^{14}C$-thymidine (52 mCi/mmol, 50 $\mu$Ci/ul, Amersham) is added to each well. The plates are incubated overnight in the same incubator and then counted on the Wallac Microbeta counter. The data is averaged to calculate an IC50 and % inhibition @ 1 $\mu$M for the antagonist mode. For the agonist mode, an EC50 and percent of maximum E2 stimulation and concentration of maximum stimulation is calculated.

TABLE

| Cmpnd (Ex. No.) | $K_i$ (ER$\alpha$) | $K_i$ (ER$\beta$) | IC50 (MCF7) | Ishikawa EC50 | Agonist % Eff | Antagonist % Eff |
|---|---|---|---|---|---|---|
| 3 | 2.47 | 8.03 | 587 | 262 | 117 | −0.2 |
| 4* | 0.91 | 3.21 | 488 | 161 | 36 | 40 |

*signifies the trifluoroacetic acid (TFA) salt

General Rat Preparation Procedure

Seventy-five day old (unless otherwise indicated) female Sprague Dawley rats (weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.2°±1.7° C. with a minimum relative humidity of 40%. The photoperiod in the room was 12 hours light and 12 hours dark.

Dosing Regimen Tissue Collection: After a one week acclimation period (therefore, two weeks post-OVX) daily dosing with a compound of formula (I) ("F-I") is initiated. 17$\alpha$-ethynyl estradiol or F-I is given orally, unless otherwise stated, as a suspension in 1% carboxymethylcellulose or dissolved in 20% cyclodextrin. Animals are dosed daily for 4 days. Following the dosing regimen, animals are weighed and anesthetized with a ketamine:Xylazine (2:1, v:v) mixture and a blood sample is collected by cardiac puncture. The animals are then sacrificed by asphyxiation with $CO_2$, the uterus is removed through a midline incision, and a wet uterine weight is determined. 17$\alpha$-ethynyl estradiol is obtained from Sigma Chemical Co., St. Louis, Mo.

Uterine Eosinophil Peroxidase (EPO) Assay

The uteri from above are kept at 4° C. until time of enzymatic analysis. The uteri are then homogenized in 50 volumes of 50 mM Tris buffer (pH-8.0) containing 0.005% Triton X-100. Upon addition of 0.01% hydrogen peroxide and 10 mM O-phenylenediamine (final concentrations) in Tris buffer, increase in absorbance is monitored for one minute at 450 nm. The presence of eosonophils in the uterus is an indication of estrogenic activity of a compound. The maximal velocity of a 15 second interval is determined over the initial, linear portion of the reaction curve.

Inhibition of Bone Loss (Osteoporosis) Test Procedure

Following the general preparation procedure described above, the rats are treated daily for thirty-five days (6 rats per treatment group) and sacrificed by carbon dioxide asphyxiation on the 36th day. The thirty-five day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized X-rays generated and analyzed by an image analysis program (NIH image) at the distal metaphysis. The proximal aspect of the tibiae from these animals are also scanned by quantitative computed tomography. In accordance with the above procedures, F-I or ethynyl estradiol ($EE_2$) in 20% hydroxypropyl β-cyclodextrin are orally administered to test animals. F-I is also useful in combination with estrogen or progestin.

Uterine Fibrosis Test Procedures

Test 1: Between 3 and 20 women having uterine fibrosis are administered F-I. The amount of compound administered is from 0.1 to 1000 mg/day, and the period of administration is 3 months. The women are observed during the period of administration, and up to 3 months after discontinuance of administration, for effects on uterine fibrosis.

Test 2: The same procedure is used as in Test 1, except the period of administration is 6 months.

Test 3: The same procedure is used as in Test 1, except the period of administration is 1 year.

Test 4: Prolonged estrogen stimulation is used to induce leiomyomata in sexually mature female guinea pigs. Animals are dosed with estradiol 3–5 times per week by injection for 2–4 months or until tumors arise. Treatment consisting of F-I or vehicle is administered daily for 3–16 weeks and then animals are sacrificed and the uteri harvested and analyzed for tumor regression.

Test 5: Tissue from human leiomyomas are implanted into the peritoneal cavity and/or uterine myometrium of sexually mature, castrated, female, nude mice. Exogenous estrogen is supplied to induce growth of the explanted tissue. In some cases, the harvested tumor cells are cultured in vitro prior to implantation. Treatment consisting of F-I or vehicle is supplied by gastric lavage on a daily basis for 3–16 weeks and implants are removed and measured for growth or regression. At the time of sacrifice, the uteri are harvested to assess the status of the organ.

Test 6: Tissue from human uterine fibroid tumors is harvested and maintained, in vitro, as primary non-transformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, F-I, and vehicle. Levels of steroid hormone receptors are assessed weekly to determine whether important cell characteristics are maintained in vitro. Tissue from 5–25 patients is utilized.

Test 7: F-I's ability to inhibit estrogen-stimulated proliferation of leiomyoma-derived ELT cell lines is measured substantially as described in Fuchs-Young, et al., "Inhibition of Estrogen-Stimulated Growth of Uterine Leiomyomas by Selective Estrogen Receptor Modulators", Mol. Car., 17(3): 151–159 (1996), the teachings of which are herein incorporated by reference.

Endometriosis Test Procedures

Test 1: Twelve to thirty adult CD strain female rats are used as test animals. They are divided into three groups of equal numbers. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. In addition, females in Group 2 have the ovaries removed. On the day following surgery, animals in Groups 1 and 2 receive intraperitoneal injections of water for 14 days whereas animals in Group 3 receive intraperitoneal injections of 1.0 mg of F-I per kilogram of body weight for the same duration. Following 14 days of treatment, each female is sacrificed and the endometrial explants, adrenals, remaining uterus, and ovaries, where applicable, are removed and prepared for histological examination. The ovaries and adrenals are weighed.

Test 2: Twelve to thirty adult CD strain female rats are used as test animals. They are divided into two equal groups. The estrous cycle of all animals is monitored. On the day of proestrus, surgery is performed on each female. Females in each group have the left uterine horn removed, sectioned into small squares, and the squares are loosely sutured at various sites adjacent to the mesenteric blood flow. Approximately 50 days following surgery, animals assigned to Group 1 receive intraperitoneal injections of water for 21 days whereas animals in Group 2 receive intraperitoneal injections of 1.0 mg of F-I per kilogram of body weight for the same duration. Following 21 days of treatment, each female is sacrificed and the endometrial explants and adrenals are removed and weighed. The explants are measured as an indication of growth. Estrous cycles are monitored.

Test 3: Autographs of endometrial tissue are used to induce endometriosis in rats and/or rabbits. Female animals at reproductive maturity undergo bilateral oophorectomy, and estrogen is supplied exogenously thus providing a specific and constant level of hormone. Autologous endometrial tissue is implanted in the peritoneum of 5–150 animals and estrogen supplied to induce growth of the explanted tissue. Treatment consisting of a compound of the present invention is supplied by gastric lavage on a daily basis for 3–16 weeks, and implants are removed and measured for growth or regression. At the time of sacrifice, the intact horn of the uterus is harvested to assess status of endometrium.

Test 4: Tissue from human endometrial lesions is implanted into the peritoneum of sexually mature, castrated, female, nude mice. Exogenous estrogen is supplied to induce growth of the explanted tissue. In some cases, the harvested endometrial cells are cultured in vitro prior to implantation. Treatment consisting of F-I supplied by gastric lavage on a daily basis for 3–16 weeks, and implants are removed and measured for growth or regression. At the time of sacrifice, the uteri are harvested to assess the status of the intact endometrium.

Test 5: Tissue from human endometrial lesions is harvested and maintained in vitro as primary non-transformed cultures. Surgical specimens are pushed through a sterile mesh or sieve, or alternately teased apart from surrounding tissue to produce a single cell suspension. Cells are maintained in media containing 10% serum and antibiotic. Rates of growth in the presence and absence of estrogen are determined. Cells are assayed for their ability to produce complement component C3 and their response to growth factors and growth hormone. In vitro cultures are assessed for their proliferative response following treatment with progestins, GnRH, F-I, and vehicle. Levels of steroid hormone receptors are assessed weekly to determine whether important cell characteristics are maintained in vitro. Tissue from 5–25 patients is utilized.

Use of Formula (1) Compound in Conjunction with Estrogen

Peri- and post-menopausal women often undergo hormone replacement therapy (HRT) to combat negative consequences associated with the drop in circulating endogenous estrogen, e.g., to treat hot flashes. However, HRT has been associated with increased risks of certain cancers including uterine and breast cancer. F-I may be employed in conjunction with HRT to inhibit these risks.

Prevention of Breast Cancer

This invention also relates to the administration of F-I to a recipient who is at risk of developing de novo breast cancer. The term "de novo", as used herein, means the lack of transformation or metamorphosis of normal breast cells to cancerous or malignant cells in the first instance. Such a transformation may occur in stages in the same or daughter cells via an evolutionary process or may occur in a single, pivotal event. This de novo process is in contrast to the metastasis, colonization, or spreading of already transformed or malignant cells from the primary tumor site to new locations.

A person who is at no particular risk of developing breast cancer is one who may develop de novo breast cancer, has no evidence or suspicion of the potential of the disease above normal risk, and who has never had a diagnosis of having the disease. The greatest risk factor contributing to the development of breast carcinoma is a personal history of suffering from the disease, or an earlier occurrence of the disease, even if it is in remission with no evidence of its presence. Another risk factor is family history of the disease.

Induction of mammary tumors in rats by administration of the carcinogen N-nitroso-N-methylurea is a well-accepted animal model for the study of breast cancer and has been found suitable for analyzing the effect of chemopreventive agents.

In two separate studies, 55-day old female Sprague-Dawley rats are given an intravenous (Study 1) or intraperitoneal (Study 2) dose of 50 mg of N-nitroso-N-methylurea per kilogram of body weight one week prior to feeding ad libitum a diet into which varying amounts of F-I, (Z)-2-[4-(1,2-diphenyl-1-butenyl)phenoxy]-N,N-dimethylethanamine base (tamoxifen base), or control are blended.

In Study 1, the dietary doses of 60 mg/kg of diet and 20 mg/kg of diet translates into roughly comparable doses of 3 and 1 mg/kg of body weight for the test animals.

In Study 2, the dietary doses of 20, 6, 2, and 0.6 mg/kg of diet translates roughly into comparable doses of 1, 0.3, 0.1 and 0.03 mg/kg of body weight for the test animals.

Rats are observed for evidence of toxicity and are weighed and palpated for tumor formation once a week. The animals are sacrificed after thirteen weeks (Study 1) or eighteen weeks (Study 2) and tumors are confirmed and weighed at autopsy.

Therapeutic Methods of Use and Dosages

The present invention also provides a method of inhibiting a disease associated with estrogen deprivation and a method for inhibiting a disease associated with an aberrant physiological response to endogenous estrogen which comprises the aforementioned method using compounds of Formula I and optionally comprises administering to a patient an effective amount of estrogen or progestin. These treatments are particularly useful for treating osteoporosis and lowering serum cholesterol because the patient will receive the benefits of each pharmaceutical agent while the compounds of the present invention would inhibit undesirable side-effects of estrogen and progestin. Activity of these combination treatments in any of the post-menopausal tests, infra, indicates that the combination treatments are useful for alleviating the symptoms of post-menopausal symptoms in women.

Various forms of estrogen and progestin are commercially available. Estrogen-based agents include, for example, ethynyl estrogen (0.01–0.03 mg/day), mestranol (0.05–0.15 mg/day), and conjugated estrogenic hormones such as Premarin® (Wyeth-Ayerst; 0.3–2.5 mg/day). Progestin-based agents include, for example, medroxyprogesterone such as Provera® (Upjohn; 2.5–10 mg/day), norethylnodrel (1.0–10.0 mg/day), and nonethindrone (0.5–2.0 mg/day). A preferred estrogen-based compound is Premarin®, and norethylnodrel and norethindrone are preferred progestin-based agents.

The method of administration of each estrogen- and progestin-based agent is consistent with that which is known in the art. For the majority of the methods of the present invention, compounds of Formula I are administered continuously, from 1 to 3 times daily. However, cyclical therapy may especially be useful in the treatment of endometriosis or may be used acutely during painful attacks of the disease. In the case of restenosis, therapy may be limited to short (1–6 months) intervals following medical procedures such as angioplasty.

As used herein, the term "patient" refers to a warm-blooded animal or mammal which is in need of inhibiting a disease associated with estrogen deprivation or in need of inhibiting a disease associated with an aberrant physiological response to endogenous estrogen. It is understood that guinea pigs, dogs, cats, rats, mice, hamsters, and primates, including humans, are examples of patients within the scope of the meaning of the term. Preferred patients include humans. Most preferred patients include postmenopausal female humans.

As used herein, the term "inhibit" is defined to include its generally accepted meaning which includes preventing, prohibiting, restraining, and slowing, stopping or reversing progression, or severity, and holding in check and/or treating existing characteristics. The present method includes both medical therapeutic and/or prophylactic treatment, as appropriate.

The term "estrogen deprivation" is meant to imply the condition where the optimal level of estrogen is absent. This level varies from one tissue to another depending on the function of the tissue. Thus, in some cases, estrogen deprivation may be the total absence of estrogen, whereas in other cases, deprivation may involve estrogen levels which are too low for proper tissue function. In human women, the two most common causes of estrogen deprivation are menopause and ovariectomy, although other conditions can be causative. Estrogen deprivation can lead to conditions including osteoporosis and cardiovascular effects such as hyperlipidemia, proliferation of aortal smooth muscle cells (restenosis), decrease in nitric oxide production (hypertension) and decrease in production of the enzyme PAI-1 (Plasminogen Activator Inhibitor-1), i.e. thrombosis.

Reduction or amelioration of other pathologies associated with menopause such as urinary incontinence, vaginal dryness, increase in the incidence of auto-immune disease, and loss of skin tone, may also be achieved by administering compounds of Formula I.

In addition to their usefulness in treating conditions associated with estrogen deprivation following menopause, the compounds of the present invention are also useful in the treatment of disease states associated with inappropriate response to endogenous estrogen in tissues both prior to and subsequent to menopause.

One example of a pathological condition associated with abnormal cellular responses to endogenous estrogen in tissues is estrogen dependent breast cancer. Estrogen dependent breast tumor cells proliferate in the presence of estrogen and the treatment of this disease has been to stop all action of estrogen on these cells.

Another estrogen dependent pathology is uterine fibrosis (uterine fibroid disease). Essentially, uterine fibrosis is a condition where there is a deposition of fibroid tissue on the wall of the uterus. This condition is a cause of dysmenorrhea and infertility in women. The exact cause of this condition is poorly understood but evidence suggests that it is an inappropriate response of fibroid tissue to estrogen. The most common treatment of uterine fibrosis involves surgical procedures both costly and sometimes a source of complications such as the formation of abdominal adhesions and infections.

Yet another disease in this category is endometriosis, a condition of severe dysmenorrhea, which is accompanied by severe pain, bleeding into the endometrial masses or peritoneal cavity and often leads to infertility. The cause of the symptoms of this condition appear to be ectopic endometrial growths located in inappropriate tissues which respond inappropriately to hormonal control.

As used herein, the term "therapeutically effective amount" means an amount of compound of the present invention which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose for human use will contain a nontoxic dosage level of from about 1 mg to about 600 mg/day of a compound of the present invention. Preferred daily doses generally will be from about 15 mg to about 300 mg/day. Most preferred doses range may constitute 10 mg, 20 mg, 30 mg, 40 mg, 50 mg, 60 mg, 70 mg, 80 mg, 90 mg, and 100 mg, administered once to three times per day.

The compounds of this invention can be administered by a variety of routes including oral, rectal, transdermal, subucutaneus, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula 1, or a pharmaceutically acceptable salt thereof, optionally containing an effective amount of estrogen or progestin, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention can be prepared by procedures known in the art using well known and readily available ingredients. For example, the compounds of formula I, with or without an estrogen or progestin compound, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds are well suited to formulation as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I, alone or in combination with a pharmaceutical agent of the present invention, generally will be administered in a convenient formulation.

What is claimed is:

1. A method for inhibiting osteoporosis comprising administering to a patient in need thereof a therapeutically effective amount of a compound of the formula

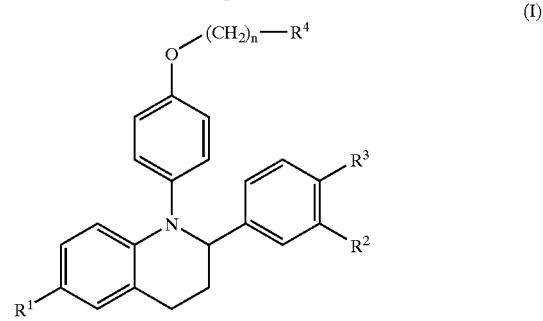

(I)

wherein
R$^1$ is —H, —OH, —O(C$_1$–C$_4$ alkyl), —OCOC$_6$H$_5$, —OCO(C$_1$–C$_6$ alkyl), or —OSO$_2$(C$_2$–C$_6$ alkyl);
R$^2$ and R$^3$ are each independently —H, —OH, —O(C$_1$–C$_4$ alkyl), —OCOC$_6$H$_5$, —OCO(C$_1$–C$_6$ alkyl), —OSO$_2$(C$_2$–C$_6$ alkyl) or halo;
R$^4$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;
n is 1, 2 or 3;
or a pharmaceutically acceptable salt thereof.

2. A method according to claim 1 wherein n is 2, or a pharmaceutically acceptable salt thereof.

3. A method according to claim 2 wherein R$^1$ is —OH, or a pharmaceutically acceptable salt thereof.

4. A method according to claim 3 wherein R$^4$ is 1-piperidinyl, or a pharmaceutically acceptable salt thereof.

5. A method according to claim 1 wherein one of R$^2$ or R$^3$ is —OH, or a pharmaceutically acceptable salt thereof.

6. A method according to claim 4 wherein one of $R^2$ or $R^3$ is —OH, or a pharmaceutically acceptable salt thereof.

7. A method according to claim 4 wherein one of $R^2$ and $R^3$ is —H or a pharmaceutically acceptable salt thereof.

8. A method according to claim 1 wherein the compound of formula I is selected from the group consisting of:
   6-methoxy-2-(4-methoxyphenyl)-1-[4-(2-piperidin-1-yl-ethyoxy)-phenyl]-1,2,3,4-tetrahydro-quinoline;
   6-methoxy-2-(4-methoxyphenyl)-1-[4-(2-pyrrolidin-1-yl-ethyoxy)-phenyl]-1,2,3,4-tetrahydro-quinoline;
   1-(4-hydroxyphenyl)-1-[4-(2-piperidin-1-yl-ethyoxy)-phenyl]-1,2,3,4-tetrahydro-quinolin-6-ol; and
   1-(4-hydroxyphenyl)-1-[4-(2-pyrrolidin-1-yl-ethyoxy)-phenyl]-1,2,3,4-tetrahydro-quinolin-6-ol; or a pharmaceutically acceptable salt thereof.

9. A method according to claim 1 wherein said compound of formula I is 1-(4-hydroxy-phenyl)-1-[4-(2-piperidin-1-yl-ethoxy)-phenyl]-1,2,3,4-tetrahydro-quinolin-6-ol, or a pharmaceutically acceptable salt thereof.

10. A method according to claim 1 wherein said compound of formula I is 1-(4-hydroxy-phenyl)-1-[4-(2-pyrrolidin-1-yl-ethoxy)-phenyl]-1,2,3,4-tetrahydro-quinolin-6-ol, or a pharmaceutically acceptable salt thereof.

11. A method according to claim 1 wherein said patient is a human.

12. A method according to claim 11 wherein the human is a postmenopausal female.

13. A method according to claim 1 wherein the compound is administered prophylactically.

14. A method for inhibiting a disease selected from estrogen dependent breast cancer, endometriosis and uterine fibrosis comprising administering to a patient in need thereof a therapeutically effective amount of a compound of the formula

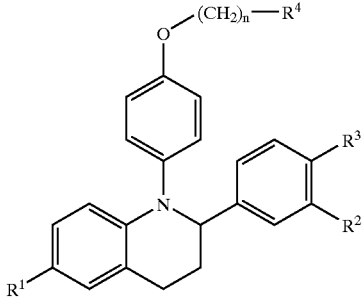

(I)

wherein
$R^1$ is —H, —OH, —O($C_1$-$C_4$ alkyl), —OCOC$_6$H$_5$, —OCO($C_1$-$C_6$ alkyl), or —OSO$_2$($C_2$-$C_6$ alkyl);
$R^2$ and $R^3$ are each independently —H, —OH, —O($C_1$-$C_4$ alkyl), —OCOC$_6$H$_5$, —OCO($C_1$-$C_6$ alkyl), —OSO$_2$($C_2$-$C_6$ alkyl) or halo;
$R^4$ is 1-piperidinyl, 1-pyrrolidinyl, methyl-1-pyrrolidinyl, dimethyl-1-pyrrolidinyl, 4-morpholino, dimethylamino, diethylamino, diisopropylamino, or 1-hexamethyleneimino;
n is 1, 2 or 3;
or a pharmaceutically acceptable salt thereof.

15. A method according to claim 14 wherein n is 2, or a pharmaceutically acceptable salt thereof.

16. A method according to claim 15 wherein $R^1$ is —OH, or a pharmaceutically acceptable salt thereof.

17. A method according to claim 16 wherein $R^4$ is 1-piperidinyl, or a pharmaceutically acceptable salt thereof.

18. A method according to claim 17 wherein one of $R^2$ or $R^3$ is —OH, or a pharmaceutically acceptable salt thereof.

19. A method according to claim 17 wherein one of $R^2$ and $R^3$ is —H or a pharmaceutically acceptable salt thereof.

20. A method according to claim 14 wherein one of $R^2$ or $R^3$ is —OH, or a pharmaceutically acceptable salt thereof.

21. A method according to claim 14 wherein the compound of formula I is selected from the group consisting of:
   6-methoxy-2-(4-methoxyphenyl)-1-[4-(2-piperidin-1-yl-ethyoxy)-phenyl]-1,2,3,4-tetrahydro-quinoline;
   6-methoxy-2-(4-methoxyphenyl)-1-[4-(2-pyrrolidin-1-yl-ethyoxy)-phenyl]-1,2,3,4-tetrahydro-quinoline;
   1-(4-hydroxyphenyl)-1-[4-(2-piperidin-1-yl-ethyoxy)-phenyl]-1,2,3,4-tetrahydro-quinolin-6-ol; and
   1-(4-hydroxyphenyl)-1-[4-(2-pyrrolidin-1-yl-ethyoxy)-phenyl]-1,2,3,4-tetrahydro-quinolin-6-ol; or a pharmaceutically acceptable salt thereof.

22. A method according to claim 14 wherein said compound of formula I is 1-(4-hydroxy-phenyl)-1-[4-(2-piperidin-1-yl-ethoxy)-phenyl]-1,2,3,4-tetrahydro-quinolin-6-ol, or a pharmaceutically acceptable salt thereof.

23. A method according to claim 14 wherein said compound of formula I is 1-(4-hydroxy-phenyl)-1-[4-(2-pyrrolidin-1-yl-ethoxy)-phenyl]-1,2,3,4-tetrahydro-quinolin-6-ol, or a pharmaceutically acceptable salt thereof.

24. A method according to claim 14 wherein said patient is a human.

25. A method according to claim 24 wherein the human is a postmenopausal female.

26. A method according to claim 14 wherein the compound is administered prophylactically.

27. A method according to claim 14 wherein said disease is estrogen-dependent breast cancer.

28. A method according to claim 27 wherein the compound of formula I is selected from the group consisting of:
   6-methoxy-2-(4-methoxyphenyl)-1-[4-(2-piperidin-1-yl-ethyoxy)-phenyl]-1,2,3,4-tetrahydro-quinoline;
   6-methoxy-2-(4-methoxyphenyl)-1-[4-(2-pyrrolidin-1-yl-ethyoxy)-phenyl]-1,2,3,4-tetrahydro-quinoline;
   1-(4-hydroxyphenyl)-1-[4-(2-piperidin-1-yl-ethoxy)-phenyl]-1,2,3,4-tetrahydro-quinolin-6-ol; and
   1-(4-hydroxyphenyl)-1-[4-(2-pyrrolidin-1-yl-ethoxy)-phenyl]-1,2,3,4-tetrahydro-quinolin-6-ol; or a pharmaceutically acceptable salt thereof.

29. A method according to claim 14 wherein the disease is endometriosis.

30. A method according to claim 29 wherein the compound of formula I is selected from the group consisting of:
   6-methoxy-2-(4-methoxyphenyl)-1-[4-(2-piperidin-1-yl-ethyoxy)-phenyl]-1,2,3,4-tetrahydro-quinoline;
   6-methoxy-2-(4-methoxyphenyl)-1-[4-(2-pyrrolidin-1-yl-ethyoxy)-phenyl]-1,2,3,4-tetrahydro-quinoline;
   1-(4-hydroxyphenyl)-1-[4-(2-piperidin-1-yl-ethoxy)-phenyl]-1,2,3,4-tetrahydro-quinolin-6-ol; and
   1-(4-hydroxyphenyl)-1-[4-(2-pyrrolidin-1-yl-ethoxy)-phenyl]-1,2,3,4-tetrahydro-quinolin-6-ol; or a pharmaceutically acceptable salt thereof.

31. A method according to claim 14 wherein the disease is uterine fibrosis.

32. A method according to claim 31 wherein the compound of formula I is selected from the group consisting of:
   6-methoxy-2-(4-methoxyphenyl)-1-[4-(2-piperidin-1-yl-ethyoxy)-phenyl]-1,2,3,4-tetrahydro-quinoline;
   6-methoxy-2-(4-methoxyphenyl)-1-[4-(2-pyrrolidin-1-yl-ethyoxy)-phenyl]-1,2,3,4-tetrahydro-quinoline;
   1-(4-hydroxyphenyl)-1-[4-(2-piperidin-1-yl-ethoxy)-phenyl]-1,2,3,4-tetrahydro-quinolin-6-ol; and
   1-(4-hydroxyphenyl)-1-[4-(2-pyrrolidin-1-yl-ethoxy)-phenyl]-1,2,3,4-tetrahydro-quinolin-6-ol; or a pharmaceutically acceptable salt thereof.

* * * * *

UNITED STATES PATENT AND TRADEMARK OFFICE
CERTIFICATE OF CORRECTION

PATENT NO. : 6,962,928 B2
DATED : November 8, 2005
INVENTOR(S) : Owen Brendan Wallace It is certified that error appears in the above-identified patent and that said Letters Patent is hereby corrected as shown below:

Title page, Item [54] and Column 1, lines 1-4,
Title, delete "TETRAHYDROQUINTLINE DERIVATIVES FOR THE INHIBITION OF OSTEOPOROSIS, ESTROGEN DEPENDENT BREAST CANCER, ENDOMETRIOSIS AND UTERINE FIBROSIS" and insert
-- TETRAHYDROQUINOLINE DERIVATIVES FOR THE INHIBITION OF DISEASES ASSOCIATED WITH ESTROGEN DEPRIVATION OR WITH AN ABERRANT PHYSIOLOGICAL RESPONSE TO ENDOGENOUS ESTROGEN --.

Signed and Sealed this

Twenty-seventh Day of December, 2005

JON W. DUDAS
*Director of the United States Patent and Trademark Office*